(12) United States Patent
Obara et al.

(10) Patent No.: US 10,752,708 B2
(45) Date of Patent: Aug. 25, 2020

(54) CURABLE COMPOSITION, CURED PRODUCT AND OPTICAL MEMBER

(71) Applicants: NIKON CORPORATION, Tokyo (JP); ESSILOR INTERNATIONAL, Charenton-le-Pont (FR)

(72) Inventors: Hideki Obara, Kawasaki (JP); Toshiaki Murai, Gifu (JP); Guillaume Cantagrel, Kuki (JP)

(73) Assignees: NIKON CORPORATION, Tokyo (JP); ESSILOR INTERNATIONAL, Charenton-le-Pont (FR)

( * ) Notice: Subject to any disclaimer, the term of this patent is extended or adjusted under 35 U.S.C. 154(b) by 119 days.

(21) Appl. No.: 16/146,766

(22) Filed: Sep. 28, 2018

(65) Prior Publication Data

US 2019/0071522 A1 Mar. 7, 2019

Related U.S. Application Data

(63) Continuation of application No. PCT/JP2016/001836, filed on Mar. 30, 2016.

(51) Int. Cl.
| | |
|---|---|
| C08F 12/30 | (2006.01) |
| C08F 12/32 | (2006.01) |
| C08F 12/24 | (2006.01) |
| C08K 3/00 | (2018.01) |
| C08L 33/14 | (2006.01) |
| C08F 12/34 | (2006.01) |
| C08F 212/14 | (2006.01) |
| C08F 212/36 | (2006.01) |
| C07C 323/16 | (2006.01) |
| C09D 133/14 | (2006.01) |
| C07C 323/12 | (2006.01) |
| C07C 323/17 | (2006.01) |
| C08F 12/36 | (2006.01) |
| C08F 20/38 | (2006.01) |
| G02B 1/04 | (2006.01) |

(52) U.S. Cl.
CPC ............ *C08F 12/30* (2013.01); *C07C 323/12* (2013.01); *C07C 323/16* (2013.01); *C07C 323/17* (2013.01); *C08F 12/24* (2013.01); *C08F 12/32* (2013.01); *C08F 12/34* (2013.01); *C08F 12/36* (2013.01); *C08F 20/38* (2013.01); *C08F 212/14* (2013.01); *C08F 212/36* (2013.01); *C08K 3/00* (2013.01); *C08L 33/14* (2013.01); *C09D 133/14* (2013.01); *G02B 1/04* (2013.01); *C07C 2603/74* (2017.05)

(58) Field of Classification Search
USPC ....... 560/222; 568/55, 58; 524/852; 526/289
See application file for complete search history.

(56) References Cited

U.S. PATENT DOCUMENTS

| | | | | |
|---|---|---|---|---|
| 3,442,955 A | * | 5/1969 | Newallis | C07C 321/00 568/56 |
| 2006/0241302 A1 | * | 10/2006 | Kubota | C07C 317/14 546/194 |
| 2015/0353667 A1 | * | 12/2015 | Ponrathnam | G02B 1/043 524/547 |

FOREIGN PATENT DOCUMENTS

| | | |
|---|---|---|
| EP | 1640366 A1 | 3/2006 |
| JP | 2014-221866 A | 11/2014 |
| WO | 2005000798 A1 | 1/2005 |

OTHER PUBLICATIONS

Oct. 29, 2019 Extended Search Report issued in European Patent Application No. 16 89 6686.9.
XP-002794971. Database Registry. Chemical Abstracts Service. Sep. 29, 1989.
Akio Kamimura et al., "Lewis Acid Induced Nucleophilic Substitution Reaction of B-Nitro Sulfides". Journal of Organic Chemistry. vol. 54. No. 21. pp. 4998-5003. Oct. 1, 1989.
Jun. 28, 2016 International Search Report issued in International Application No. PCT/JP2016/001836.
Jun. 28, 2016 Written Opinion issued in International Application No. PCT/JP2016/001836.
Toashiaki Murai et al.; "Sequential One-Pot Addition of Excess Aryl-Grignard Reagents and Electrophiles to O-Alkyl Thioformates"; Chemistry A European Journal; 2013; vol. 19; No. 39; pp. 13112-13119.
Mariola Zielinska-Blajet et al.; "Simple approach to modular chiral scaffolds: binding functional sulfur nucleophiles to Cinchona alkaloids"; Tetrahedron; 2016; vol. 72; pp. 2643-2648.

* cited by examiner

*Primary Examiner* — Fred M Teskin
(74) *Attorney, Agent, or Firm* — Oliff PLC

(57) ABSTRACT

A curable composition capable of manufacturing a cured product having a high refractive index is provided. The curable composition contains a polymerizable compound represented by formula (1) and inorganic particles. In formula (1), $L_a$ represents a divalent linking group, and the divalent linking group includes at least one of a divalent aromatic group, a divalent polycyclic aliphatic group and an alkylene group having an aromatic group, Ar represents an aromatic group, and R represents an aromatic group optionally having one or more substituents or a polycyclic aliphatic group optionally having one or more substituents.

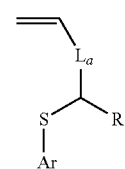

Formula (1)

19 Claims, No Drawings

CURABLE COMPOSITION, CURED PRODUCT AND OPTICAL MEMBER

CROSS-REFERENCE TO RELATED APPLICATIONS

This application is a Continuation of PCT International Application No. PCT/JP2016/001836 filed on Mar. 30, 2016. The above application is hereby expressly incorporated by reference, in its entirety, into the present application.

TECHNICAL FIELD

The present invention relates to a curable composition, a cured product and an optical member.

BACKGROUND ART

Resin ingredient-containing optical members such as plastic lenses are light in weight, are excellent in moldability and workability, and are high in safety, and hence have rapidly become widespread in a variety of fields.

Various proposals have been made on such resin ingredient-containing optical members. For example, PTL 1 proposes a material containing metal oxide particles.

CITATION LIST

Patent Literature

[PTL 1] JP 2014-221866 A

SUMMARY OF INVENTION

Development of a material having a higher refractive index has been required to meet the demand for further reductions in thickness and weight of optical members. For example, the material described in PTL 1 does not meet the higher level recently required and a further improvement has been needed.

The present invention has been made in view of the above and an object of the present invention is to provide a curable composition capable of manufacturing a cured product having a high refractive index.

Another object of the present invention is to provide a cured product obtained by using the curable composition. Still another object of the present invention is to provide an optical member obtained by using the curable composition.

Still another object of the present invention is to provide a polymerizable compound.

The inventors of the present invention have made an intensive study on the problem in the conventional technology, and as a result found that the problem can be solved by using a curable composition containing a specific polymerizable compound and inorganic particles.

Specifically, the inventors of the present invention have found that the foregoing objects can be achieved by the characteristic features as described below.

(1) A curable composition comprising: a polymerizable compound represented by formula (1) to be described later; and inorganic particles.

(2) The curable compound according to (1), wherein the polymerizable compound represented by formula (1) to be described later is a polymerizable compound represented by formula (2) to be described later.

(3) The curable composition according to (2), wherein the polymerizable compound represented by formula (2) to be described later satisfies at least one of following requirements 1 and 2:

requirement 1: $L_c$ represents an alkylene group having a hydroxy group;

requirement 2: R represents a polycyclic aliphatic group having a hydroxy group.

(4) The curable composition according to any one of (1) to (3), wherein the inorganic particles comprise at least one type selected from the group consisting of metal oxide particles and metal sulfide particles.

(5) A cured product obtained by curing the curable composition according to any one of (1) to (4).

(6) An optical member obtained by curing the curable composition according to any one of (1) to (4).

(7) A polymerizable compound represented by formula (1) to be described later.

(8) The polymerizable compound according to (7) which is represented by formula (2) to be described later.

(9) The polymerizable compound according to (8), satisfying at least one of following requirements 1 and 2:

requirement 1: $L_c$ represents an alkylene group having a hydroxy group;

requirement 2: R represents a polycyclic aliphatic group having a hydroxy group.

DESCRIPTION OF EMBODIMENTS

A curable composition, a cured product and an optical member are described below in detail with reference to preferred embodiments.

In the specification, a numerical range indicated with a hyphen (-) should include the upper limit value and the lower limit value. For example, a numerical range of 10-20 includes 10 and 20.

The curable composition is characterized by the use of a polymerizable compound having a specific structure of high refractive index fragments. Sulfur atom as well as an aromatic group and/or a polycyclic aliphatic group are contained in the polymerizable compound at predetermined positions, whereby the polymerizable compound itself exhibits a high refractive index, resulting in an increased refractive index of a cured product as well.

Further, the polymerizable compound has a specific structure, whereby the dispersibility of inorganic particles in the cured product is improved and the cured product also has excellent transparency. In particular, as will be described later in detail, by containing a polar group, in particular a hydroxy group or an ester group in the polymerizable compound, the effects are more excellent.

The curable composition contains at least a polymerizable compound represented by formula (1) to be described later and inorganic particles.

Respective ingredients contained in the curable composition are described below in detail.

(Polymerizable Compound Represented by Formula (1))

The curable composition contains a polymerizable compound represented by formula (1).

[Chem. 1]

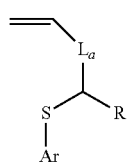

Formula (1)

In formula (1), $L_a$ represents a divalent linking group, and the divalent linking group includes at least one of a divalent aromatic group, a divalent polycyclic aliphatic group and an alkylene group having at least an aromatic group.

The divalent linking group is not particularly limited as long as at least one of a divalent aromatic group, a divalent polycyclic aliphatic group, and an alkylene group having at least an aromatic group is included. Examples of the divalent linking group include a divalent aromatic group, a divalent polycyclic aliphatic group, a divalent monocyclic aliphatic group, an alkylene group, an alkenylene group, an alkynylene group, a divalent non-aromatic heterocyclic group, —O—, —S—, —SO$_2$—, —NR$_L$—, —CO—, —COO—, —CONR$_L$—, —SO$_3$—, —SO$_2$NR$_L$—, and groups obtained by combining two or more thereof (e.g., alkyleneoxy group, alkyleneoxycarbonyl group, and alkylenecarbonyloxy group). $R_L$ as used herein represents a hydrogen atom or an alkyl group (preferably having 1 to 10 carbon atoms). Divalent linking groups including a polar group are particularly suitable. Examples of polar groups include —SO$_2$—, —NR$_L$—, —CO—, —COO—, —CONR$_L$—, —SO$_3$—, —SO$_2$NR$_L$—.

The divalent linking group may have a substituent (the divalent linking group may be substituted with a substituent). Examples of the substituent include a hydroxy group, an alkyl group, an alkenyl group, an alkynyl group, an aromatic group (e.g., an aryl group), an alkoxy group, a nitro group, a halogen atom, an amino group, an acylamino group, and a cyano group.

As a polar group, hydroxy group is particularly suitable as substituent.

The divalent linking group may have one or more substituents.

As described above, the divalent linking group includes at least one of a divalent aromatic group, a divalent polycyclic aliphatic group and an alkylene group having at least an aromatic group. These groups are also referred to as specific linking groups. In other words, the divalent linking group may be composed of only a specific linking group or of a combination of a specific linking group with other groups.

When the divalent linking group is a combination of a specific linking group with other groups, preferred examples of such other groups include —COO—, —CONR$_L$—, and an alkylene group which may have a substituent (e.g., a hydroxy group).

Examples of the divalent aromatic group include a divalent aromatic hydrocarbon group and a divalent aromatic heterocyclic group. The divalent aromatic hydrocarbon group means a group obtained by removing two hydrogen atoms directly attached to an aromatic ring from an aromatic hydrocarbon compound, examples thereof including phenylene group, anthrylene group, phenanthrylene group, and pyrenediyl group. The divalent aromatic heterocyclic group means a group obtained by removing two hydrogen atoms directly attached to a heterocyclic ring from an aromatic heterocyclic compound, examples thereof including thiophenediyl group, benzothiadiazolediyl group, furandiyl group, pyridinediyl group, and pyrrolediyl group.

The divalent polycyclic aliphatic group (divalent condensed polycyclic aliphatic hydrocarbon group) means a group obtained by removing two hydrogen atoms directly attached to a polycyclic aliphatic ring from a polycyclic aliphatic compound. The polycyclic aliphatic compound is a compound that contains no aromatic ring but a ring in which two or more aliphatic rings are condensed. Examples thereof include adamantane, norbornane, bicyclo[2.1.0]pentane, bicyclo[2.1.1]hexane, bicyclo[2.2.0]hexane, bicyclo[3.1.0]hexane, norpinane, norcarane, bicyclo[2.2.2]octane, bicyclo[3.2.1]octane, bicyclo[3.3.0]octane, bicyclo[4.2.0]octane, bicyclo[5.1.0]octane, bicyclo[4.3.0]nonane, and tricyclo[5.2.1.0$^{2,6}$]decane.

The number of carbon atoms contained in the divalent polycyclic aliphatic group is not particularly limited, and preferably 5-30, more preferably 6-20, and even more preferably 7-15.

Specific examples of the divalent polycyclic aliphatic group include groups to be illustrated below which are obtained by removing two hydrogen atoms from adamantane as a polycyclic aliphatic compound. Two hydrogen atoms may be removed from one carbon atom as in the left side structural formula.

Alternatively, two hydrogen atoms may be removed from different carbon atoms as in the right side structural formula. In the following formulas, * represents a bonding position.

[Chem. 2]

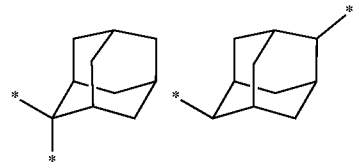

The number of carbon atoms in an alkylene group moiety in the alkylene group having at least an aromatic group (alkylene group which may be substituted with at least an aromatic group) is not particularly limited, and is preferably 1-15, more preferably 1-10, and even more preferably 1-3.

The aromatic group may have a monocyclic structure or a polycyclic structure. Specific examples of the aromatic group include a monovalent aromatic hydrocarbon group (monocyclic aromatic hydrocarbon group, polycyclic aromatic hydrocarbon group) and a monovalent aromatic heterocyclic group (monocyclic aromatic heterocyclic group, polycyclic aromatic heterocyclic group). Examples of the monovalent aromatic hydrocarbon group include phenyl group, naphthyl group, anthryl group, azulenyl group, acenaphthenyl group, fluorenyl group, phenanthryl group, and pyrenyl group. Examples of the monovalent aromatic heterocyclic group include pyridyl group, pyrimidinyl group, furyl group, pyrrolyl group, imidazolyl group, benzimidazolyl group, pyrazolyl group, pyrazinyl group, oxazolyl group, benzoxazolyl group, thiazolyl group, isoxazolyl group, isothiazolyl group, furazanyl group, thienyl group, quinolyl group, benzofuryl group, dibenzofuryl group, benzothienyl group, dibenzothienyl group, indolyl group, and carbazolyl group.

The number of aromatic groups substituted for the alkylene group is not particularly limited and may be one or more than one. The number of aromatic groups is preferably more than one in terms of a higher refractive index of the cured product (hereinafter also referred to simply as "in terms of more excellent effect of the invention").

Ar represents an aromatic group. The definition of the aromatic group is the same as that of the aromatic group described on the alkylene group having an aromatic group as mentioned above, and examples of the aromatic group include a monovalent aromatic hydrocarbon group and a monovalent aromatic heterocyclic group, and a monovalent aromatic hydrocarbon group is preferred.

R represents an aromatic group which may have one or more substituents (an aromatic group which may be substituted with one or more substituents) and a polycyclic aliphatic group (monovalent polycyclic aliphatic group) which may have one or more substituents (a polycyclic aliphatic group which may be substituted with one or more substituents).

The definition of the aromatic group is the same as that of the aromatic group described on the alkylene group having an aromatic group as mentioned above, and examples of the aromatic group include a monovalent aromatic hydrocarbon group and a monovalent aromatic heterocyclic group, and a monovalent aromatic hydrocarbon group is preferred.

The polycyclic aliphatic group represented by R refers to a group (monovalent group) obtained by removing one hydrogen atom directly attached to a polycyclic aliphatic ring from a polycyclic aliphatic compound. The polycyclic aliphatic compound is as defined above and specific examples thereof include illustrative compounds described as specific examples on the foregoing divalent polycyclic aliphatic group.

The number of carbon atoms contained in the polycyclic aliphatic group is not particularly limited, and preferably 5-30, more preferably 6-20, and even more preferably 7-15.

The aromatic group and the polycyclic aliphatic group represented by R may have a substituent. Examples of the substituent include a hydroxy group, an alkyl group, an alkenyl group, an alkynyl group, an alkoxy group, a nitro group, a halogen atom, an amino group, an acylamino group, and a cyano group. As a polar group, hydroxy group is particularly suitable as substituent. The number of substituents is not particularly limited and is one or more than one.

Specific examples of the polycyclic aliphatic group having one or more substituents include the following: One carbon atom may have a substituent (hydroxy group) together with a bonding arm as in the left side structural formula or different carbon atoms may have a bonding arm and a substituent, respectively, as in the right side structural formula. The bonding arm refers to a bonding moiety that is connected to another structure and in the following formulas, * represents a bonding position.

[Chem. 3]

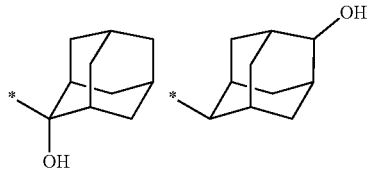

Of these, in terms of more excellent effect of the invention, a preferred embodiment of the polymerizable compound represented by formula (1) is a polymerizable compound containing a polar group, in particular a hydroxy substituent or an ester group. Of these, in terms of more excellent effect of the invention, a preferred embodiment of the polymerizable compound represented by formula (1) is a polymerizable compound represented by formula (2).

In the polymerizable compound represented by formula (2), $L_a$ in formula (1) corresponds to -$L_b$-$L_c$-. $L_b$ is linked to the double bond side.

[Chem. 4]

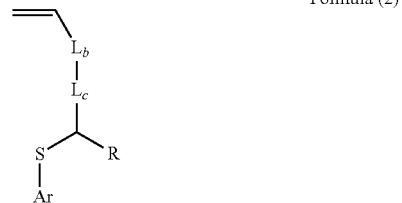

Formula (2)

In formula (2), $L_b$ represents a divalent aromatic hydrocarbon group or —COO— (ester group). The definition of the divalent aromatic hydrocarbon group is the same as that of the divalent aromatic hydrocarbon group described on the divalent linking group as mentioned above. The bonding mode of —COO— is not particularly limited and a bonding arm *1 represented by *1-COO-*2 is preferably bound to a double bond moiety.

$L_c$ represents a single bond, an alkylene group having at least a hydroxy group, an alkylene group having at least an aromatic group, or a divalent polycyclic aliphatic group.

The number of carbon atoms in an alkylene group moiety in the alkylene group having at least a hydroxy group is not particularly limited, and is preferably 1-15, more preferably 1-10, and even more preferably 1-3.

The definition of the alkylene group having at least an aromatic group is the same as that of the alkylene group having at least an aromatic group that was described on the divalent linking group as mentioned above.

The definition of the divalent polycyclic aliphatic group is the same as that of the divalent polycyclic aliphatic group described on the divalent linking group as mentioned above.

In formula (2), when $L_b$ is —COO—, $L_c$ represents an alkylene group having at least an aromatic group or a divalent polycyclic aliphatic group.

The definitions of Ar and R in formula (2) are the same as those of Ar and R in formula (1), respectively.

Of these, in terms of more excellent effect of the invention, the polymerizable compound represented by formula (2) preferably satisfies at least one of the following requirements 1 and 2. When at least one of the requirements 1 and 2 is satisfied, the polymerizable compound contains hydroxy group to enhance the interactivity with inorganic particles to be described later, thereby improving the dispersibility of the inorganic particles, resulting in more excellent refractive index and transparency of the cured product.

Requirement 1: $L_c$ represents an alkylene group having a polar group, in particular a hydroxy group.

Requirement 2: R represents a polycyclic aliphatic group having a polar group, in particular a hydroxy group.

The method of synthesizing the polymerizable compound represented by formula (1) is not particularly limited and the polymerizable compound can be synthesized by combining known synthesis methods.

The curable composition may contain only one type of polymerizable compound represented by formula (1) or two or more types of polymerizable compounds represented by formula (1).

(Inorganic Particles)

The curable composition contains inorganic particles.

Exemplary types of the inorganic particles include metal oxide particles, metal sulfide particles, and metal particles, and at least one type selected from the group consisting of metal oxide particles and metal sulfide particles is preferred in terms of more excellent refractive index and more excellent transparency of the cured product. Two or more types of particles selected from the group consisting of metal oxide particles, metal sulfide particles and metal particles may be used in mixture as the inorganic particles.

Particles of an oxide of at least one type of metal selected from Al, Sn, Sb, Ta, Ce, La, Nb, Fe, Zn, W, Zr, In, and Ti are preferably used as the metal oxide particles. Of these, Ta-containing oxide particles (tantalum oxide), Zr-containing oxide particles (zirconium oxide particles) and Ti-containing oxide particles (titanium oxide particles) are preferred in terms of their high refractive index.

Particles of a sulfide of at least one type of metal selected from Zn, Ag, Se, Fe, Pb, Sb, Cd, Cr, Co, Zr, Sn, Ti, Ni, Mg, Mo, La, Pd, Y, In, and Ir are preferably used as the metal sulfide particles. Of these, ZnS is preferred.

The metal oxide particles may contain only one type of metal (metal atom) or more than one type of metal (metal atom) selected from those illustrated above.

The shape of the inorganic particles is not particularly limited and exemplary shapes include a spherical shape, an ellipsoidal shape, a polyhedral shape and a scale-like shape.

The average particle size of the inorganic particles is not particularly limited and is preferably 1-200 nm and more preferably 2-30 nm. When the average particle size is within the above range, the curable composition is excellent in dispersion stability.

The average particle size can be determined by dynamic light scattering.

The surface of each inorganic particle may be surface-modified with a predetermined compound. In other words, the inorganic particles to be used may be coated inorganic particles, the surfaces of which are coated with a predetermined compound. Surface modification with a predetermined compound allows a predetermined functional group (e.g., hydroxy group) to be introduced into the surface of an inorganic particle, whereby the inorganic particle having the predetermined functional group (e.g., hydroxy group) on its surface is obtained.

(Optional Ingredients)

The curable composition may contain other ingredients in addition to the above-described polymerizable compound represented by formula (1) and inorganic particles.

Optional ingredients that may be contained in the curable composition are described below in detail.

The curable composition may contain a polymerizable compound other than the above-described polymerizable compound represented by formula (1) (hereinafter also referred to simply as "another polymerizable compound."

A known polymerizable compound can be used as another polymerizable compound and a radical polymerizable compound is preferred in terms of reactivity.

In terms of the strength of the cured product, a polyfunctional polymerizable compound is preferred and a polyfunctional radical polymerizable compound is more preferred as another polymerizable compound. Examples of the polyfunctional radical polymerizable compound that may be preferably illustrated include those having two or more ethylenically unsaturated double bond groups selected from the group consisting of acryloyloxy group, methacryloyloxy group, acrylamide group, methacrylamide group, vinyloxy group, and N-vinyl group. Examples of such another polymerizable compound include polyfunctional acrylic monomers such as polyfunctional (meth)acrylamides and polyfunctional (meth)acrylates, and polyfunctional vinyl monomers such as divinylbenzene.

The curable composition may contain a polymerization initiator. A most suitable known polymerization initiator can be used based on the polymerization form and examples of the polymerization initiator include a photopolymerization initiator and a thermal polymerization initiator.

More specific examples thereof include aromatic ketones, acylphosphine oxides, oxime esters, quinones, benzoin ethers, 2,4,5-triaryl imidazole dimers, acridine derivatives, and N-phenylglycines.

The curable composition may contain a solvent. The solvent may be water, an organic solvent and mixture thereof.

The type of the organic solvent is not particularly limited and examples thereof include alcohol solvents such as methanol and ethanol; ketone solvents such as acetone, methyl ethyl ketone, cyclohexanone, 2-heptanone, and 3-heptanone; ether solvents such as diethyl ether, tetrahydrofuran, and ethylene glycol dimethyl ether; ester solvents such as methyl acetate, butyl acetate, benzyl benzoate, dimethyl carbonate, ethylene carbonate, gamma-butyrolactone, and caprolactone; hydrocarbon solvents such as benzene, toluene, ethylbenzene, and tetralin; halogenated hydrocarbon solvents such as dichloromethane, trichloroethane, and chlorobenzene; amide or cyclic amide solvents such as N,N-dimethylformamide, N,N-dimethylacetamide, and N-methylpyrrolidone (N-methyl-2-pyrrolidone); sulfone solvents such as dimethyl sulfone; and sulfoxide solvents such as dimethyl sulfoxide.

The curable composition may further optionally contain various additives such as a light stabilizer, a UV absorber, an antioxidant, a coloration preventing agent, a dye, a filler, and an internal release agent.

(Curable Composition)

The curable composition contains at least the above-described polymerizable compound represented by formula (1) and inorganic particles.

The amount of the compound represented by formula (1) to be contained in the curable composition is not particularly limited, and is preferably 5-90 wt %, more preferably 10-70 wt %, and even more preferably 15-50 wt % with respect to the total solids weight because the cured product has a higher refractive index and the curable composition has more excellent dispersion stability.

The term "solids" refers to ingredients that may make up a cured product to be described later, as exemplified by the compound represented by formula (1) and the inorganic particles, and no solvent is included. An ingredient that may make up a cured product is included in the solids even if it has a liquid property.

The amount of the inorganic particles to be contained in the curable composition is not particularly limited, and is preferably 1-80 wt %, more preferably 10-70 wt %, and even more preferably 20-60 wt % with respect to the total solids weight because the cured product has a higher refractive index and the curable composition has more excellent handleability.

When contained in the curable composition, another polymerizable compound is preferably contained in an amount of 5-80 wt % and more preferably 10-60 wt % with respect to the total solids weight.

When contained in the curable composition, a polymerization initiator is preferably contained in an amount of 0.01-10 wt % and more preferably 0.1-5 wt % with respect to the total solids weight.

The curable composition may contain a solvent (for example, the solvent content of the curable composition is from 0 to 30 wt %) but its content is preferably small. To be more specific, a solvent is preferably contained in an amount of up to 5 wt % with respect to the total weight of the composition and is more preferably not contained substantially.

The method of preparing the curable composition is not particularly limited and the curable composition can be prepared by mixing the above-described ingredients using a known method. Moreover, an inorganic particle-containing dispersion may be prepared in advance, and the compound represented by formula (1) is subsequently added thereto.
(Cured Product, Optical Member)

A cured product obtained by polymerizing the above-described curable composition is optically transparent and has a desired refractive index because the inorganic particles are uniformly dispersed in the cured product.

The method of curing the curable composition is not particularly limited and a known curing method is applied. For example, photo-curing and heat curing are used and photo-curing is preferred in terms of its excellent productivity.

Conditions at the time of photo-curing are not particularly limited and optimal conditions are selected as appropriate for the materials to be used. As energy rays for use in photo-curing, alpha rays, gamma rays, electron rays, X-rays, ultraviolet rays, visible rays and infrared rays can be used, and ultraviolet rays are preferred.

The curing treatment may include a plurality of treatments performed under different curing conditions.

The cured product obtained by the curing treatment has a high refractive index and hence can be suitably used as an optical member.

Examples of the optical member include optical lenses such as an eyeglass lens, and a camera lens; optical films such as a polarizing film, a polarizer protective film, a phase difference film, a light diffusion film, a viewing angle expansion film, a reflective film, an anti-reflective film, an anti-glare film, and a brightness enhancement film; and a prism sheet; and a microlens array. Of these, an eyeglass lens, a camera lens and films suitable for lamination on an eyeglass lens or a camera lens are particularly preferable.

The curable composition can also be applied to form a coating film. In other words, the curable composition can also be used to form a coating film on a target object. The thickness of the coating film is not particularly limited and is, for example, about 1 nm-10 mm.

EXAMPLES

The present invention is described below more specifically by way of examples. However, the present invention should not be construed as being limited to the following examples.

Synthesis Example 1: Compound 1

Into a two-necked flask with a volume of 20 mL were introduced benzyl(phenyl)sulfane (0.60 g, 3.0 mmol) and tetrahydrofuran (THF) (6.0 mL), and the mixture was cooled to −78° C. To this solution was added n-butyllithium (1.56 M hexane solution, 2.019 mL, 3.15 mmol) and the mixture was stirred for 1 hour. To the resulting solution was further added a solution of 4-vinylbenzaldehyde (0.4 g, 3.0 mmol) in THF (9.0 mL) and the mixture was stirred for 3 hours. During the reaction, the reaction temperature gradually increased to −30° C. The resulting reaction solution was poured into ice water and extracted with diethyl ether three times. The resulting diethyl ether solution was washed with water. Further, magnesium sulfate was added to remove water in the solution. Then, the magnesium sulfate was removed by filtration. The filtrate was concentrated and subjected to silica gel column chromatography (hexane: ethyl acetate=10:1) to separate a compound 1 (0.79 g) shown below.

[Chem. 5]

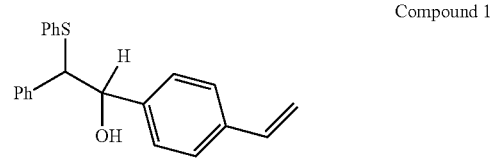

Compound 1

Synthesis Example 2: Compound 2

Into a two-necked flask with a volume of 20 mL were introduced benzyl(phenyl)sulfane (0.60 g, 3.0 mmol) and THF (4.0 mL), and the mixture was cooled to −78° C. To this solution was added n-butyllithium (1.56 M hexane solution, 2.019 mL, 3.15 mmol) and the mixture was stirred for 1 hour. To the resulting solution was further added a solution of 2-adamantanone (0.451 g, 3.0 mmol) in THF (6.0 mL) and the mixture was stirred for 7 hours. During the reaction, the reaction temperature gradually increased to −30° C. The resulting reaction solution was poured into ice water and extracted with diethyl ether three times. The resulting diethyl ether solution was washed with water. Further, magnesium sulfate was added to remove water in the solution. Then, the magnesium sulfate was removed by filtration. The filtrate was concentrated and subjected to silica gel column chromatography (hexane: ethyl acetate=30:1) to separate an intermediate 1 (0.86 g) shown below.

[Chem. 6]

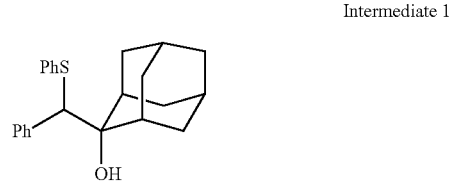

Intermediate 1

Into a two-necked flask with a volume of 20 mL were introduced the intermediate 1 (0.18 g, 0.5 mmol) and THF (5.0 mL) at 0° C. To this solution was added n-butyllithium (1.56 M hexane solution, 0.51 mL, 0.8 mmol) and the mixture was stirred at 0° C. for 15 minutes. To the resulting solution was further added acryloyl chloride (0.081 mL, 0.5 mmol) and the mixture was stirred at room temperature for 1 hour. The resulting reaction solution was poured into ice water and extracted with diethyl ether three times. The resulting diethyl ether solution was washed with water.

Further, magnesium sulfate was added to remove water in the solution. Then, the magnesium sulfate was removed by filtration. The filtrate was concentrated and subjected to silica gel column chromatography (hexane: ethyl acetate=10:1) to separate a compound 2 (0.19 g) shown below.

[Chem. 7]

Compound 2

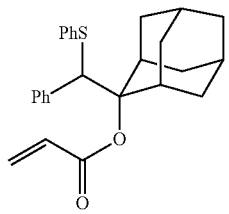

Synthesis Example 3: Compound 3

Into a two-necked flask with a volume of 50 mL were introduced benzyl(phenyl)sulfane (2.0 g, 10.0 mmol) and THF (12.0 mL), and the mixture was cooled to −78° C. To this solution was added n-butyllithium (1.56 M hexane solution, 6.82 mL, 10.5 mmol) and the mixture was stirred for 1 hour. To the resulting solution was further added a solution of benzophenone (1.82 g, 10.0 mmol) in THF (18.0 mL) and the mixture was stirred for 7 hours. During the reaction, the reaction temperature gradually increased to −30° C. The resulting reaction solution was poured into ice water and extracted with diethyl ether three times. The resulting diethyl ether solution was washed with water. Further, magnesium sulfate was added to remove water in the solution. Then, the magnesium sulfate was removed by filtration. The filtrate was concentrated and subjected to silica gel column chromatography (hexane: ethyl acetate=20:1) to separate an intermediate 2 (3.50 g) shown below.

[Chem. 8]

Intermediate 2

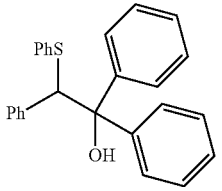

Into a two-necked flask with a volume of 20 mL were introduced the intermediate 2 (1.91 g, 5.0 mmol) and THF (50.0 mL) at 0° C. To this solution was added n-butyllithium (1.54 M hexane solution, 4.54 mL, 7.0 mmol) and the mixture was stirred at 0° C. for 15 minutes. To the resulting solution was further added acryloyl chloride (0.81 mL, 5.0 mmol) and the mixture was stirred at room temperature for 1 hour. The resulting reaction solution was poured into ice water and extracted with diethyl ether three times. The resulting diethyl ether solution was washed with water. Further, magnesium sulfate was added to remove water in the solution. Then, the magnesium sulfate was removed by filtration. The filtrate was concentrated and subjected to silica gel column chromatography (hexane: ethyl acetate=10:1) to separate a compound 3 (0.59 g) shown below.

[Chem. 9]

Compound 3

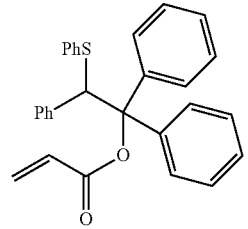

Synthesis Example 4: Compound 4

An intermediate 3 shown below was synthesized according to the procedure described in Eur. J. Org. Chem. 2011, 4693.

[Chem. 10]

Intermediate 3

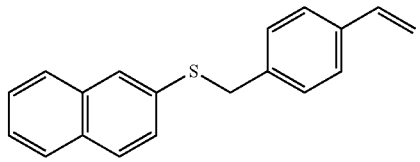

Into a two-necked flask with a volume of 20 mL were introduced the intermediate 3 (0.275 g, 1.0 mmol) and THF (10.0 mL) and the mixture was cooled to −78° C. To this solution was added n-butyllithium (1.56 M hexane solution, 0.70 mL, 1.2 mmol) and the mixture was stirred at −78° C. for 1 hour. To the resulting solution was further added a solution of 2-adamantanone (0.15 g, 1.0 mmol) in THF (0.6 mL) and the mixture was stirred at −30° C. overnight. The resulting reaction solution was poured into ice water and extracted with diethyl ether three times. The resulting diethyl ether solution was washed with water. Further, magnesium sulfate was added to remove water in the solution. Then, the magnesium sulfate was removed by filtration. The filtrate was concentrated and subjected to silica gel column chromatography (hexane:ethyl acetate: dichloromethane=10:1:1) to separate a compound 4 (0.36 g) shown below.

[Chem. 11]

Compound 4

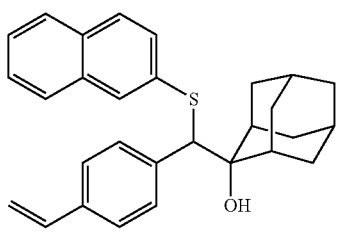

Synthesis Example 5: Compound 5

Into a two-necked flask with a volume of 20 mL were introduced the intermediate 3 (0.553 g, 2.0 mmol) and THF (20.0 mL) and the mixture was cooled to −78° C. To this solution was added n-butyllithium (1.56 M hexane solution, 1.70 mL, 2.4 mmol) and the mixture was stirred at −78° C. for 1 hour. To the resulting solution was further added a solution of 4-vinylbenzaldehyde (0.25 mL, 2.0 mmol) in THF (0.8 mL) and the mixture was stirred at −30° C. overnight. The resulting reaction solution was poured into ice water and extracted with diethyl ether three times. The resulting diethyl ether solution was washed with water. Further, magnesium sulfate was added to remove water in the solution. Then, the magnesium sulfate was removed by filtration. The filtrate was concentrated and subjected to silica gel column chromatography (hexane: ethyl acetate=10:1) to separate a compound 5 (0.50 g) shown below.

[Chem. 12]

Compound 5

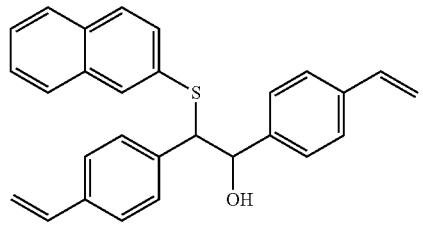

The structure of each of the compounds 1 to 5 was identified by $^1$H NMR and $^{13}$C NMR.

Example 1

A solution of zirconium oxide particles (Sakai Chemical Industry Co., Ltd.; trade name: SZR-M; 30 wt % methanol solution; average particle size: 3-5 nm), the foregoing compound 1, divinylbenzene, and Irgacure 184 (registered trademark; manufactured by BASF) were mixed to obtain a mixture solution. Next, an evaporator was used to distill off methanol from the resulting mixture.

In the resulting mixture, the weight ratio among the zirconium oxide particles, the compound 1, the divinylbenzene and Irgacure 184 in the mixture solution (zirconium oxide particles:compound 1:divinylbenzene:Irgacure 184) was 25.6:30.6:42.7:1.1.

Then, the resulting mixture was inserted between two glass sheets disposed at a distance of 0.5 mm and irradiated with ultraviolet light (amount of irradiation energy: 40,000 mJ/cm$^2$) to obtain a cured product.

The cured product was visually transparent. As a result of measurement of the refractive index and the transmittance of the cured product according to Measurement of Refractive Index and Measurement of Transmittance to be described below, the refractive index at a wavelength of 594 nm was 1.65 and the transmittance at a wavelength of 500 nm was 70.7%. These results confirmed that the resulting cured product has a high refractive index and is also excellent in transmittance.

(Various Evaluations)

The cured product obtained above was subjected to the following evaluations.

(Measurement of Refractive Index)

The refractive index of the resulting cured product was measured with a prism coupler model 2010 manufactured by Metricon Corporation. The measurement wavelength was 594 nm.

(Measurement of Transmittance)

The transmittance of the resulting cured product was measured with a spectrophotometer U4100 manufactured by Hitachi High-Technologies Corporation. The transmittance shown above is at a wavelength of 500 nm.

Comparative Example 1

The procedure of Example 1 was repeated except that the compound 1 was not used and the weight ratio among zirconium oxide particles, divinylbenzene, and Irgacure 184 (zirconium oxide particles:divinylbenzene:Irgacure 184) was changed to 28.1:71.1:0.8, thereby preparing a cured product. The resulting cured product was visually opaque, and the refractive index and the transmittance could not be measured.

The refractive index in each of the compounds 1 to 5 was calculated by simulation using ChemSketch manufactured by ACD/Labs and as a result the refractive index of each compound was as follows:

TABLE 1

| | Compound 1 | Compound 2 | Compound 3 | Compound 4 | Compound 5 |
|---|---|---|---|---|---|
| Refractive index | 1.66 | 1.63 | 1.66 | 1.68 | 1.69 |

The measured value of the refractive index (wavelength: 594 nm) of the compound 1 was 1.64 and the refractive index of each of the compounds as obtained by simulation is substantially the same as the measured value.

The cured product obtained by using the compound 1 in Example 1 as mentioned above had a high refractive index. Meanwhile, in consideration of the results of the simulation, each of the compounds 2 to 5 exhibits a refractive index which is at the same level as that of the compound 1 and cured products having a high refractive index would be obtained by replacing the compound 1 with the compounds 2 to 5, respectively.

The invention claimed is:

1. A curable composition comprising:
a polymerizable compound represented by formula (1):

Formula (1)

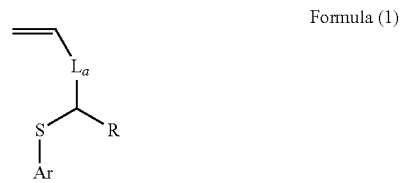

where La represents a divalent linking group, and the divalent linking group includes at least one of a divalent aromatic group, a divalent polycyclic aliphatic group and an alkylene group having at least an aromatic group, Ar represents an aromatic group, and R represents an aromatic group optionally having one or more substituents or a polycyclic aliphatic group optionally having one or more substituents; and inorganic particles.

2. The curable compound according to claim 1, wherein the polymerizable compound represented by formula (1) is a polymerizable compound represented by formula (2):

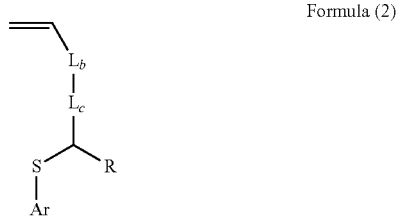

Formula (2)

where Lb represents a divalent aromatic hydrocarbon group or COO—,
Lc represents a single bond, an alkylene group having at least a hydroxy group, an alkylene group having at least an aromatic group, or a divalent polycyclic aliphatic group, and when Lb is —COO—, Lc represents an alkylene group having at least an aromatic group or a divalent polycyclic aliphatic group, and
definitions of Ar and R in formula (2) are identical to definitions of Ar and R in formula (1), respectively.

3. The curable composition according to claim 2, wherein the polymerizable compound represented by formula (2) satisfies at least one of following requirements 1 and 2:
requirement 1: Lc represents an alkylene group having a hydroxy group;
requirement 2: R represents a polycyclic aliphatic group having a hydroxy group.

4. The curable composition according to claim 1, wherein the inorganic particles comprise at least one type selected from the group consisting of metal oxide particles and metal sulfide particles.

5. A cured product obtained by curing the curable composition according to claim 1.

6. An optical member obtained by curing the curable composition according to claim 1.

7. A polymerizable compound represented by formula (2):

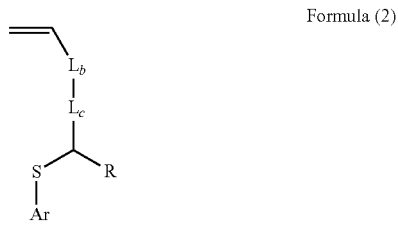

Formula (2)

where Lb represents a divalent aromatic hydrocarbon group or COO—,
Lc represents a single bond, an alkylene group having at least a hydroxy group, an alkylene group having at least an aromatic group, or a divalent polycyclic aliphatic group, and when Lb is —COO—, Lc represents an alkylene group having at least an aromatic group or a divalent polycyclic aliphatic group,
Ar represents an aromatic group, and
R represents an aromatic group optionally having one or more substituents or a polycyclic aliphatic group optionally having one or more substituents.

8. The polymerizable compound according to claim 7, satisfying at least one of following requirements 1 and 2:
requirement 1: Lc represents an alkylene group having a hydroxy group;
requirement 2: R represents a polycyclic aliphatic group having a hydroxy group.

9. The curable composition according to claim 2, wherein the inorganic particles comprise at least one type selected from the group consisting of metal oxide particles and metal sulfide particles.

10. The curable composition according to claim 3, wherein the inorganic particles comprise at least one type selected from the group consisting of metal oxide particles and metal sulfide particles.

11. A cured product obtained by curing the curable composition according to claim 2.

12. A cured product obtained by curing the curable composition according to claim 3.

13. A cured product obtained by curing the curable composition according to claim 4.

14. A cured product obtained by curing the curable composition according to claim 9.

15. A cured product obtained by curing the curable composition according to claim 10.

16. An optical member obtained by curing the curable composition according to claim 2.

17. An optical member obtained by curing the curable composition according to claim 3.

18. An optical member obtained by curing the curable composition according to claim 4.

19. An optical member obtained by curing the curable composition according to claim 9.

* * * * *